United States Patent
Schweizer

(10) Patent No.: US 11,310,347 B2
(45) Date of Patent: Apr. 19, 2022

(54) TRANSFERRING A USER INTERFACE

(71) Applicant: Siemens Healthcare GmbH, Erlangen (DE)

(72) Inventor: Hans Schweizer, Plattling (DE)

(73) Assignee: Siemens Healthcare GmbH, Erlangen (DE)

(*) Notice: Subject to any disclaimer, the term of this patent is extended or adjusted under 35 U.S.C. 154(b) by 120 days.

(21) Appl. No.: 16/809,000

(22) Filed: Mar. 4, 2020

(65) Prior Publication Data

US 2020/0287993 A1  Sep. 10, 2020

(30) Foreign Application Priority Data

Mar. 4, 2019  (EP) ..................... 19160516

(51) Int. Cl.
| | | |
|---|---|---|
| *G06F 15/16* | (2006.01) | |
| *H04L 67/131* | (2022.01) | |
| *H04L 67/125* | (2022.01) | |
| *H04L 67/59* | (2022.01) | |
| *H04L 67/01* | (2022.01) | |
| *G16H 40/67* | (2018.01) | |

(52) U.S. Cl.
CPC ............ *H04L 67/38* (2013.01); *H04L 67/125* (2013.01); *H04L 67/2861* (2013.01); *H04L 67/42* (2013.01); *G16H 40/67* (2018.01)

(58) Field of Classification Search
CPC ... H04L 67/38; H04L 67/125; H04L 67/2861; H04L 67/42; H04L 43/0864; H04L 43/16; H04L 43/0852; H04L 67/36; H04L 67/2828; H04L 67/327; H04L 67/04; H04L 65/80; H04L 67/025; H04L 67/08; H04L 67/2823; H04L 67/322; G16H 40/67; A61B 6/46; A61B 6/461; A61B 6/4441

See application file for complete search history.

(56) References Cited

U.S. PATENT DOCUMENTS

| | | | | |
|---|---|---|---|---|
| 2011/0019552 | A1* | 1/2011 | Karaoguz | H04L 45/124 370/236 |
| 2015/0103894 | A1* | 4/2015 | Diard | H04N 19/188 375/240.06 |

(Continued)

FOREIGN PATENT DOCUMENTS

DE    102014219760 A1    3/2016

OTHER PUBLICATIONS

European Search Report for European Application No. 19160516.1-1213 dated Jul. 24, 2019.

(Continued)

*Primary Examiner* — John B Walsh
(74) *Attorney, Agent, or Firm* — Lempia Summerfield Katz LLC

(57) ABSTRACT

A method is defined for transferring a user interface from at least one server via a proxy to at least one client. A user interface of the server is transferred to the client such that the user interface is displayed on the client, and the server may be controlled from the client. In order to display the user interface on the client, a data stream of a plurality of successive frames is transmitted from the server to the client by a packet-based transfer. A latency of the transfer is determined recurrently for individual frames in order to monitor the transfer. In addition, a medical device and a server are defined.

20 Claims, 5 Drawing Sheets

(56) References Cited

U.S. PATENT DOCUMENTS

| | | | |
|---|---|---|---|
| 2017/0188023 A1* | 6/2017 | Brabenac | H04N 17/02 |
| 2018/0098083 A1* | 4/2018 | Mcallister | H04N 19/103 |
| 2018/0302594 A1 | 10/2018 | Taylor | |
| 2021/0082317 A1* | 3/2021 | Hoppmann | G16H 10/60 |

OTHER PUBLICATIONS

European Office Action for European Application No. 19160516.1-1213 dated Sep. 27, 2021.
Shi, Weidong, et al. "Scalable support for 3D graphics applications in cloud." 2010 IEEE 3rd International Conference on Cloud Computing IEEE, 2010. pp. 346-353.

* cited by examiner

TRANSFERRING A USER INTERFACE

This application claims the benefit of European Patent Application No. EP 19160516.1, filed Mar. 4, 2019, which is incorporated by reference in its entirety.

BACKGROUND

The present embodiments relates to transferring a user interface.

In a hospital, it is typical to use a large number of different devices (e.g., medical devices) that are normally also made by different suppliers. Examples of such medical devices are imaging devices (e.g., C-arm machines or ultrasound devices), but also navigation devices, devices for monitoring clinical parameters of a patient, or devices for procedures on a patient. When several devices are being used in a single application (e.g., in a specific operation), a user of the devices (e.g., a surgeon or other operating-theater personnel) rely on interactions with these multiple devices. Hence, it is vital that these devices work together as smoothly as possible for a best possible clinical outcome.

The first problem is that the numerous devices are competing for the limited space in the vicinity of the patient, specifically around an operating table, because each of the devices includes one or more human-machine interfaces that are to be within reach of the user. Examples of such interfaces are monitors for display, and keyboards or mice for input, or touchscreens (e.g., special monitors both for display and for input). For the purpose of interaction, a user interface that may be used simultaneously for displaying information and for inputting control commands by an input device is normally presented on a monitor. Merging the interfaces of a plurality of devices in order to save space and reduce the display and input modalities in the region of the operating table is not readily possible because, implemented in the individual devices, usually as a result of a risk classification, are measures that are tied to the interface concerned. In addition, there is also the problem that the various devices usually have device-specific cable connections, which may present particular hygienic challenges especially in the sterile environment of a hospital and more precisely in an operating theater environment.

Delays in displaying information and in the input of control commands may have fatal consequences especially when operating medical devices. For example, in spinal surgery, the surgical instrument is navigated with the aid of a display, where time is accordingly critical to the display being accurate. For example, the insertion of a pedicle screw in a vertebra is performed, for example, by observing via a monitor, which is to accordingly display the current situation reliably because otherwise the patient may be seriously and permanently injured.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a user interface of a device is transferred, for the purpose of displaying information from the device and for the purpose of controlling the device, to another device. The aim is to transfer the user interface using technology that is as simple and inexpensive as possible while providing that the device is controlled with minimum possible risk, especially with regard to a potentially delayed transfer. For example, it is also the aim to bundle the user interfaces of a plurality of devices in order to minimize the cabling complexity especially in an operating theater.

The statements relating to the method apply, mutatis mutandis, to the medical device and to the server, and vice versa.

The method is used to transfer a user interface from at least one server via a proxy to at least one client. The proxy and all the clients are, for example, parts of the same device and, in this case, are connected to one another via at least one internal network. The device including proxy and client is also referred to as a master device. The proxy forms an interface of the device to the outside and is, in this case, connected via at least one external network to one or more other devices, each of which constitutes a server. The statements relating to embodiments that have one server or that have one client apply analogously also to embodiments that have a plurality of servers or a plurality of clients. The internal network may be a TCP/IP network. The proxy is connected between server and client, with the result that all the data being transferred from a server to a client, or vice versa, passes through the proxy. The user interface of each server may hence be presented simultaneously on each of the clients, and conversely, a plurality of servers may analogously also be controlled from a single client.

The master device is configured to perform the method and includes for this purpose, for example, a control device (e.g., a controller) that executes the method. The control device is, for example, a computer that also contains the proxy. In an embodiment, the master device is a medical device (e.g., a medical imaging device such as a C-arm machine). A medical imaging device includes at least one monitor that then, in the present case, acts as a client in order to also display one or more user interfaces of one or more servers as an alternative to, or in combination with, a user interface of the master device. A touchscreen may, for example, be provided as the client.

In an embodiment, the master device is formed from multiple components and includes a main unit and an auxiliary unit. In the case of a C-arm machine, the main unit includes a C-arm and a radiation source, as well as a main control device (e.g., the aforementioned control device) and a monitor, specifically for controlling the master device. The auxiliary unit is a side-cart in this case, which may be positioned separately from the main unit and includes one or more further monitors (e.g., for presenting frames that are acquired by the master device). The monitors of the main and auxiliary devices are each used as clients in this case. The server may likewise be a medical device, although, for example, from another manufacturer (e.g., from an outside supplier). For example, the server is a navigation device for depicting the different positions of various objects in a common coordinate system (e.g., to assist a surgeon in planning an operation). Such objects are, for example, a patient, one or more medical devices (e.g., a medical imaging device), an instrument for the treatment or for a procedure, an implant, or the like.

According to the method, a user interface of the server is transferred to the client such that the user interface is displayed on the client, and the server may be controlled from the client. It is thus possible for a user to use the client to control the server and, conversely, to transmit information from the server to the client and output the information via the client. The user interface may be a graphical user interface (GUI) and typically includes display fields for presenting information and control fields for inputting control commands. By virtue of transmitting the user interface, the user interface may be used on the client in order to control the server remotely. The specific embodiment of the user interface depends on the device. The client receives, via the user interface, an input (e.g., a control command) from a user. The input is then forwarded via the proxy to the server and processed by the server. Conversely, a visual, audible, or haptic output of the server is directed via the proxy to the client and output there to the user. Thus, interaction with the server is generally possible from the client, where "interaction" is used as a collective term to refer to both an output of information to a user and also an input by the user in order to control the device.

According to the method, in order to display the user interface on the client, a data stream of a plurality of successive frames is transmitted from the server to the client by a packet-based transfer. The frames are frames for presenting the user interface and are produced by the server. The server, for example, includes a display device for displaying the user interface for the purpose of direct control of the server. In the present case, however, the frames are transmitted to the client alternatively or additionally. This is done in the present case in the form of packets. In principle, individual frames may be transferred in a plurality of packets that are recombined after the transfer in order to obtain the frame (e.g., when using TCP/IP), which limits packets to a specified size. In the present case, however, as a simplification and without loss of generality, it is assumed that a single frame belongs to exactly one packet (e.g., that a single packet contains a single frame). The data stream accordingly includes a plurality of successive packets that are sent at a frequency equal to a frame rate of the server. A packet also includes, in addition to a frame, for example, other data (e.g., a frame number and other parameters that are presented in the description below). A packet is alternatively also referred to as a datagram.

The packet-based transfer between server and client is, for example, bidirectional. The server sends a packet including a frame and, if applicable, additional other data via the proxy to the client. After receiving the packet, the client sends a packet as a reply via the proxy to the server. The reply contains, for example, a frame number, so that the server is able to associate the reply with a previously sent packet. Server, proxy, and client are each configured to receive the packets in both directions, to analyze the packets, and, if applicable, to modify, delete, or add data.

According to the method, a latency of the transfer is determined recurrently for individual frames (e.g., for each frame) in order to monitor the transfer. This recurrent monitoring of the receipt of the individual frames (e.g., the individual packets) provides that the latency of the transfer is monitored at the frame buffer level. Since, by definition, the latency defines the time taken to transmit the frames, the latency may be determined (e.g., measured or quantified) by observing the arrival of the frame data at the client. Thus, in the present case, the transmission of a frame, or more generally of a packet, is used to determine the latency (e.g., is used recurrently), so that the latency is determined continuously. An appropriate reaction by the server, the proxy, or the client is then triggered suitably depending on the latency.

A particular advantage of the present embodiments is, for example, that the latency is measured at a frequency lying in the region of the frame rate of the server and of the client. In one embodiment, the associated latency is determined whenever a frame is received, and hence, the latency is measured frame by frame, resulting in a corresponding measurement rate. As described in detail later, in a development, the proxy reduces the frame rate instead of passing on the frame rate in full to the client, and therefore, the measurement rate may be correspondingly reduced in the case of the client determining the latency. The latency is determined at frame rates of 30 to 60 frames/s, for example, and thus, usually at an interval of a few tens of milliseconds. In general, any slowdown in the transfer may hence be detected particularly quickly, and a particularly rapid reaction thereto is accordingly possible. This is advantageous especially in the clinical environment, where delays and resultant misinformation may have particularly dramatic consequences.

Another advantage is that in the present case, the determination of the latency is defined in a protocol (e.g., by a transfer protocol), and therefore, there are no specific requirements made of the hardware. The method may be performed and is, for example, actually performed mostly or even entirely using particularly low-cost and simple standard technology. A transfer protocol may, for example, be in particular specific rules (e.g., method acts) for handling the packets by the server, the proxy, and the client, and, for example, also a specific composition of the packets. At least in the external network between server and proxy, the user interface is transferred in a wired or wireless manner via a low-cost, packet-based network (e.g., standard Ethernet, WLAN, or suchlike, and not via a special real-time Ethernet). The internal network is based, for example, on TCP or UDP technology or similar protocols that run on standard Ethernet hardware. The method, and the transfer protocol used in the method, are characterized in that monitoring of the latency is implemented solely, or at least mainly, in software, and therefore, no special hardware is required, so that low-cost standard components are used (e.g., Category 5 cable). The hardware involved (e.g., server, proxy and client) is to be designed merely to apply the transfer protocol (e.g., to execute relevant programs that bring about the execution of the method). Any window-based environments are supported by virtue of the transfer protocol working at the frame buffer level. For example, the transfer protocol is also used to transmit control commands to the server via a corresponding return channel.

The present embodiments are based initially, for example, on the observation that a simple video distribution solution is suitable in principle for transferring a user interface of one device to another device, and also for bundling a plurality of user interfaces on one device. This is done by retrieving the relevant monitor signal in hardware. There is no need to interfere with the possibly proprietary software of the device concerned, but "merely" to copy the output from this device. This solution is advantageous, for example, for devices from outside suppliers. The disadvantage with the video distribution solution, however, is the additional hardware required (e.g., additional cabling) and, by its nature, the lack of a return channel for controlling the device. In the case of a simple video distribution solution, additional cables and also additional input devices are needed for such a return channel. Thus, the transfer of the user interface of one device to another device while maintaining full functionality is not possible as part of a simple video distribution solution.

The server is configured to perform the method (e.g., in combination with a corresponding master device including proxy and client). In order to perform the method, the server includes, for example, a control device (e.g., a controller, a computer).

The frames from the server may be retrieved in software (e.g., by a server program, a dynamic Link library (DLL))

installed for this purpose on the server. In this case, this server program is used to perform the entire server-side frame-sending (e.g., consisting of reading (grabbing) the frames from a frame buffer of the server), optionally encoding the frames, and packet-based sending of the frames to the proxy and ultimately to the client. In this process, a display region of the frame buffer, which is predefined by the manufacturer, for example, is read out and sent. In one embodiment, the same server program is also used in the reverse sense to implement control of the server, by control commands being received at the server and output at the server.

In a variant, the frames from the server are retrieved by hardware but without interfering with the hardware of the server. This is achieved by connecting to the server via a video output a separate (e.g., standalone computer), on which the above-described server program is executed. The computer then thereby reads the frames from the frame buffer, if applicable, encodes the frames, and finally sends the frames via the proxy to the client. The separate computer is thus used as a non-invasive grabber.

The return channel may also be provided by the described server program on the server or on a separate computer. Control commands from the client to the server are accordingly sent via here. In the case of a separate computer being used for the retrieval by hardware, this computer is suitably connected to the server via an appropriate port for the input of control commands (e.g., via a USB port). The separate computer then behaves with respect to the server, for example, like an input device (e.g., like a keyboard or mouse).

To summarize, a bidirectional connection of server and client is advantageously achieved both with the implementation purely in software and when using a separate computer, without having to interfere with the software or the hardware of the server itself. One or more of the present embodiments include the described server program, which when executed on a server or on a separate computer connected to a server causes the server to implement the transfer protocol (e.g., to execute the acts of the method that relate to the server, in particular in association with a corresponding proxy and client). The server program is thus also considered to be part of the present embodiments.

As another example, a client program, which when executed on a master device (e.g., on a client of a master device) causes the master device to implement the transfer protocol (e.g., to execute the acts of the method that relate to the client and also to the proxy, in particular in association with a corresponding server), is provided. The client program is thus also considered to be included in the present embodiments.

The server program and the client program are each computer programs. Hence, as yet another example, a computer-readable data storage medium, on which the server program or the client program is stored, is provided.

The present embodiments are also based on the observation that remote control (e.g., based on Remote Desktop or a terminal server) is suitable for forwarding the input from one device to another device. The associated display and input are transferred via a packet-based connection, whereby it is possible to also maintain input functionality of the user interface. In this case, however, bandwidth restrictions often arise depending on the network. In addition, the network does not necessarily guarantee the reliability required, for example, with regard to delay to a display (e.g., there is no monitoring of the latency of the transfer between the devices), even though this is important, especially in the clinical environment, to providing that the display and input are live. Although special real-time network technologies (e.g., Profinet (brand name)) do provide a certain response time, the special real-time network technologies are costly and, for example, also require modifications to the hardware (e.g., the use of switches).

To summarize, a core aspect of the present embodiments is thus, for example, that latency monitoring at the frame buffer level, which is defined in a protocol, achieves particularly reliable transfer of a user interface in a simplest possible standard network.

The latency (e.g., the delay in the transfer of frame data from the server to the client) is determined in the present case in order to cause the server, the client, or the proxy thereupon to react suitably thereto. A reaction may be triggered here when the latency exceeds a specified threshold value. The latency is determined by the client, by the proxy, by the server, or by a plurality of these components. The client, the proxy, or the server obtains the information needed for this purpose from the data stream (e.g., from the individual packets).

In the present case, the latency may be determined by the client and also used by the client to suitably adjust its behavior with respect to the user. This is based on the consideration that the client displays the interface to the user and hence is sensibly used to inform the user of transfer problems and to prevent input mistakes directly.

In one embodiment, the latency is determined as the absolute frame latency (AFL) (e.g., as the difference between a start of a server-side processing of a particular frame, and the end of a client-side processing of that particular frame).

In an embodiment, when transferring a particular frame, the server also sends a time stamp that indicates a start time of the server-side processing of the frame (e.g., the start of reading the frame from a frame buffer of the server). The client-side processing of the frame is divided into a receive process and a display process for the frame, where the display process, for example, does not start until the receive process has finished. The absolute frame latency is then determined as the sum of two time segments. For example, a first time segment extends from the start time until the end of the receive process, which is denoted, for example, by an end time that is suitably ascertained. A second time segment defines a time length of the display process. The end time may be ascertained by the client itself after receipt of the particular frame. Thus, in total, the absolute frame latency includes the server-side and the client-side frame processing plus the transfer via the proxy and the networks involved.

In order to determine the absolute frame latency, the client needs information from the server end (e.g., the start time), which the server accordingly transmits with the particular frame. The client may insert the absolute frame latency or suitable parameters for determining the absolute frame latency, along with the relevant frame number in the reply to the server via the proxy, so that the server may then itself determine the absolute frame latency.

The absolute frame latency may be obtained from the following, successively executed acts and, for example, solely from the sum of the time lengths of the acts: first, a server-side read process for a frame (e.g., reading (grabbing) the frame from the frame buffer of the server); second, compressing the frame, although this is optional and is omitted in one variant; third, packet-based transfer of the frame from the server via the proxy to the client; fourth, the client receiving the frame (e.g., including additionally decoding the frame); fifth, displaying the frame on the client by suitable driving of a monitor and suitable switchover of pixels. The first and second acts are elements of the server-side processing of the frame. The third act denotes the transfer between server and client via the proxy and the various networks. The fourth and fifth acts are elements of the client-side processing of the frame, where the fourth act corresponds to the receive process of the client, and the fifth act corresponds to the display process. Each of these acts has a certain time length, and the sum of these time lengths gives the absolute frame latency.

The time length from the start of the first act to the end of the fourth act (e.g., from the start of the read process to the end of the receive process) may be calculated from the start time and the end time, and hence, for example, calculated entirely in software. In contrast, determining the time length of the fifth act (e.g., of the display process) may not be achieved readily by standard ways, because this time length normally depends, for example, on the graphics driver or display controller of the client, where, for example, the vertical synchronization or the double buffering of frames is relevant.

In a suitable embodiment, the time length of the display process is stored as a predefined offset in a memory (e.g., in a memory of the client). The offset is determined in advance, for example, by suitable tests and measurements and then stored in the memory and just retrieved when needed during operation. Hence, determining the absolute frame latency is advantageously implemented entirely in software.

In a variant that is also suitable, the client measures the time length of the display process for a particular frame. To do this, the client may be operated with a special display driver that continuously measures the time length of the display process dynamically for a particular frame (e.g., in combination with suitably adapted firmware for a display controller of the client). An activity of a backlight of a monitor (e.g., a display of the client) may be monitored in the process in order to provide that the particular frame has also actually appeared for the user. Determining the latency is hence again significantly improved and is then suitable for particularly safety-critical applications. Unlike the determination described earlier that is purely in software, in this embodiment, the determination of the absolute frame latency includes an alteration in hardware (e.g., the described modification of the client) that advantageously continues to leave the server (e.g., the device from a potential outside supplier) unaffected. Apart from this, however, in this embodiment, the determination of the absolute frame latency is implemented otherwise, for example, purely in software.

In a development, an interaction latency is determined in addition to the absolute frame latency, and, for example, precedes the previously described absolute frame latency. The interaction latency describes the time length required for an input by the user at the client to lead to a change in the user interface at the server.

When there are a plurality of clients, it is possible that different latencies also arise for the different data streams. In an embodiment, the proxy evaluates the absolute frame latencies of a plurality of clients with respect to a server, and uses a maximum comparison to determine the largest absolute frame latency, which is then transferred to the server, so that the server may react appropriately (e.g., when a largest absolute frame latency exceeds a threshold value).

The server and the client may each include a real-time clock (RTC) for determining the start time and the end time. In a suitable embodiment, for this purpose, when a connection is being established, the server initializes a monotonically incrementing counter (e.g., monotonic clock), which, for example, is also used to generate the time stamps. This implements a virtual clock, which the proxy uses for synchronization when a connection is being established and, for example, also for recurrent synchronization while the connection is in place. The proxy identifies therefrom a relative divergence of its time from the time of the server. The same applies to the client. Actual synchronization of the real-time clocks (e.g., as in network time protocol (NTP)), however, may be dispensed with.

Each relative divergence may be averaged over a plurality of measurements, so that the determination is more robust overall. This also counteracts short-term faults in the networks (e.g., asymmetric delays) that may lead to errors in the determination of the absolute frame latency. In other words, periodic time synchronization between the server, the proxy, and the client, in which instead of synchronizing the real-time clocks themselves, each of these communication nodes keeps its own local time, but the proxy and the client periodically align their times with the time of the server (e.g., by identifying the relative divergence from the virtual clock of the server), is achieved. Thus, to summarize, the described synchronization does not depend on actual clocks in the devices concerned and thus is also robust with regard to time changeovers. By virtue of the recurrent alignment, the described synchronization is also robust with regard to relative drift of the clocks. This synchronization is defined, for example, by the transfer protocol and is accordingly performed during the execution of the method.

In one embodiment, the absolute frame latency, or at least the end time at the client, is transmitted in a reply to the server, which calculates therefrom, in conjunction with a time of arrival of the reply at the server, a round-trip time for the transfer between server and client. The round-trip time is obtained, for example, as the sum of the absolute frame latency and the time taken for the reply of the client to reach the server. When there are a plurality of clients, the round-trip time is obtained, for example, from the largest of a plurality of absolute frame latencies (e.g., as the round-trip time between the server and the slowest client). The server then uses the round-trip time, for example, to derive therefrom additional information relating to the bandwidth of the transfer.

Alternatively or additionally, in determining the absolute frame latency, the latency may be determined as the relative latency between two successive frames. Thus, the relative latency is obtained, for example, as the difference between the end times, receive times, or arrival times of two successive frames at the client. The relative latency is also known for short as the inter-frame latency (IFL). The relative latency is measured at the client end (e.g., by the client itself) and may be reported back from the client to the server (e.g., after each received frame). In contrast with the absolute frame latency, the relative latency may be determined purely by the client (e.g., without additional information from the server).

The client detects, on the basis of the relative latency, for example, whether the display is being refreshed regularly or whether the transfer is frozen or halted (e.g., as a result of a slow or broken connection). In this context, a transfer rate between server and client may also be determined in order to avoid a transmission over a slow network, and in such a situation, to warn the user accordingly that the transfer rate is too low to guarantee adequate safety. An example of a slow network is a wireless network that has temporarily reduced transmission power, or a wired network containing a damaged cable.

In an embodiment, the client determines the latency, compares this latency with at least one threshold value, and outputs an indicator if the latency exceeds the threshold value. The threshold value may be adjusted appropriately and is stored, for example, in a memory of the client. For example, a semitransparent overlay of the user interface, or a text, or a combination thereof, is output as the indicator, warning that the latency has exceeded the threshold value, and the displayed user interface therefore may no longer be live. The indicator may be color-coded (e.g., in the form of traffic lights) by outputting a green indicator when the latency is acceptable, a yellow indicator when approaching the threshold value, and a red indicator when the threshold value is exceeded.

In another embodiment, the client determines the latency, compares the latency with at least one threshold value, and disables the user interface of the server on the client if the latency exceeds the threshold value. Any input via the client is thereby blocked. Corresponding input devices may be blocked for this purpose (e.g., the inputs of these devices are not forwarded to the server). This prevents a potential input mistake, for example, as a result of an input-element assignment that has changed in the meantime but is not shown owing to the latency. Also, inputs that are in progress may be interrupted if the threshold value is exceeded.

The threshold value is in general either preset and stored in a memory of the client, for example, or is specified dynamically by the server (e.g., when a connection is being established between server and client). Both variants are advantageous and may also be combined. The dynamic specification is based, for example, on the idea that the master device initially has no knowledge of what latencies are still acceptable for a server; instead this is defined by the server itself because the server manufacturer knows the specific risks and implements a commensurate risk mitigation strategy in the server. In this case, the threshold value is defined by the server and transmitted to the client by the transfer protocol (e.g., at run time, once there is an existing connection).

In general, a graduated threshold value is also advantageous. For example, the threshold value then includes a plurality of levels for the latency, for each of which, when exceeded, a different, suitable indicator (e.g., the traffic-light type indicator described above) is output, or a different, suitable action is performed, or a combination thereof. Especially fine tuning of the behavior of the server, the proxy, or the client is achieved by graded reactions using a graduated threshold value, or, more precisely, using a plurality of threshold values.

In an embodiment including a plurality of clients, the latency is detected, for example, individually for each client and hence individually for each data stream (e.g., for each individual connection between the server and the respective client). The same applies analogously in an embodiment including a plurality of servers.

An embodiment is also provided in which alternatively or additionally to the client, the proxy determines the latency, because, especially when there are a plurality of clients, the proxy is suitable for controlling the various data streams, which may have different requirements, and takes into account the particular latency in each case.

An embodiment is also provided in which one of the components determines the latency and sends the determined latency to another of the components (e.g., as part of a packet), given that the latency is linked to a specific packet. In an embodiment, the client determines the latency and transmits the latency to the server in a reply in order to allow the server to react to the latency and, for example, in order to change, and adapt to the latency, the output of the user interface based on a risk assessment. The reaction of the server is defined, for example, by the manufacturer. The same applies to the proxy determining the latency, and to corresponding forwarding to the server.

The data stream generated by a server may be too large for the client. In other words, in principle, there is a risk that the client does not support a frame rate of the server but has a lower frame rate, and therefore, the client is overloaded by the number of frames. As a result of this, the user interface may accordingly be presented incorrectly. It is also potentially possible for a receive buffer of the client to run out of space, thereby establishing a corresponding, disadvantageous latency. In order to prevent a client that has a lower performance than the server being overloaded in this way or running out of space, bandwidth control, in which the size of the data stream between server and client is controlled by the proxy, may be performed. In this process, the proxy adapts the frame rate of the server advantageously to the client as part of the bandwidth control in order to reduce the load on the client.

The bandwidth control is also advantageous in view of the fact that other data (e.g., control commands) is also usually transmitted in addition to the frame data of the user interface. In order for the internal and external networks to have a particularly low-cost design, the internal and external networks do not support, for example, any quality of service (QoS), as would be the case, for example, in a real-time network. Bandwidth control by the proxy now advantageously prevents disruption to the transfer of other data by limiting the transmission of frame data in favor of other data, with the result that the latter may be transferred particularly reliably.

Four preferred strategies for bandwidth control (e.g., specifically for limiting the frame rate) are described below (e.g., static bandwidth control, dynamic bandwidth control, bandwidth control by disabling unnecessary data streams, and bandwidth control by frame-encoding by the proxy). The dynamic bandwidth control is a closed-loop bandwidth control system, but is also referred to below by the more general term of bandwidth control. The static and dynamic strategies may be combined (e.g., to use these strategies in parallel). In one embodiment, a combination is to use the dynamic limiting as a subsidiary to the static limiting (e.g., if a defined frame rate for the client concerned is not stored in the proxy for the purpose of static limiting, and hence static limiting is not possible). The bandwidth control by disabling unnecessary data streams may be suitable in an embodiment including a plurality of servers.

In an embodiment, the server sends the frames at a frame rate that is limited by the proxy to a maximum bandwidth (e.g., of the internal network) by the proxy forwarding frames to the client within a given time segment only until the maximum bandwidth is reached, and not forwarding to the client any of the subsequent frames within the time segment. As a result, in the routing through to the client, the proxy limits the frame rate provided by the server, and generates a new, adapted, and, for example, reduced frame rate. Static limiting is thereby achieved (e.g., static in the sense of the bandwidth, whereas it is entirely possible for the number of frames per unit of time to vary). In this process, effectively a rolling summation of the volume of frame data being transferred is performed, and frames are omitted when the volume of data exceeds an upper limit (e.g., when the maximum bandwidth is reached). For example, the bandwidth is determined over a time period of 1 s for a frame rate of the server of 30 frames/s (e.g., the bandwidth of the last 30 frames is calculated). Starting from the first frame of these 30 frames, then, as many frames are forwarded until the maximum bandwidth is reached, with any remaining frames all being discarded. Given 30 frames/s, a new frame is available after 33 ms, and the process is repeated correspondingly with an offset viewing window, so that the oldest frame drops out of the summation. The discarded frames are not forwarded to the client by the proxy. If a frame is discarded, this is flagged to the server by the proxy in a reply, so that the server may react accordingly depending on the embodiment.

The maximum bandwidth defines the maximum volume of data per time segment (e.g., unit of time) that is forwarded to the client. The maximum bandwidth equals 100 Mbit/s, for example. The static bandwidth control, for example, is based on the consideration that the individual frames may sometimes differ in size because of compression, and therefore take up a varying bandwidth depending on the compression. For frames that are more highly compressed, more frames per unit of time are then forwarded to the client than for frames that are less highly compressed in order to keep within the maximum bandwidth overall. The static bandwidth control conserves not only the processing capacity of the client but also the internal network, so that other data (e.g., control commands) may still be transferred safely in parallel with the frame data, and the internal network does not run the risk of being overrun with too large a volume of frame data. For example, the bandwidth control limits the bandwidth for frame data to 50% of the bandwidth of the internal network.

An embodiment is also suitable in which the proxy reduces the frame rate of the server not to a maximum bandwidth, or not solely to a maximum bandwidth, but to a maximum frame rate of the client. The maximum frame rate equals a maximum number of frames within a defined time segment. In the case of static limiting, the first frames are transferred within this time period until the maximum number of frames for this time period is reached, and all the subsequent frames within the time period are discarded (e.g., are not transferred). For example, if the maximum frame rate of the client equals 30 frames/s, and the server sends frame data at a frame rate of 40 frames/s, then per second only the first 30 frames are transferred, and the remaining 10 frames are not. This strategy is particularly suitable both for preventing an overload of the internal network and also for clients that have a particularly limited processing capacity (e.g., a monitor of the main device of a multicomponent C-arm machine). In the case of such clients, the limiting to a maximum frame rate then provides at every point in time that the received frame data does not overload the processing capacity of the client.

The static limiting may be performed in a client-specific manner (e.g., separately for each client). In one embodiment, the maximum frame rate is adjustable and is set by the proxy to suit the client. The maximum frame rate is stored in a memory of the proxy.

In another suitable embodiment, the frames from the server are forwarded by the proxy at a frame rate that is adapted dynamically by ascertaining a round-trip time between the server and the client, and depending on the round-trip time, forwarding only a subset of frames to the client. This achieves dynamic limiting, in which the frame rate is adapted dynamically to a, for example, varying, processing capacity of the client. The round-trip time (RTT) has already been described above and equals the sum of the time taken to transfer a frame from the server to the client and the time taken for the client to reply to the server. If the round-trip time exceeds a defined upper threshold value, the frame rate is reduced; if the round-trip time goes below a different, lower threshold rate, the frame rate is increased.

Thus, the round-trip time acts as feedback for closed-loop control of the bandwidth. An increasing round-trip time, for example, signals that an input buffer of the client is running out of space, and therefore, in this case, the frame rate is reduced. Conversely, a falling round-trip time signals spare capacity in the client. The same applies analogously to the available bandwidth of the internal network. This strategy thus provides overall optimum adaptation of the frame rate to the instantaneous workload and hence to the instantaneously available processing capacity of the client, and to the available bandwidth of the internal network, thereby achieving overall a highest possible frame rate. This is suitable for a client (e.g., a standalone client) that has an especially high processing capacity (e.g., a monitor of the auxiliary device of a multicomponent C-machine).

In a suitable embodiment, the round-trip time is determined by the proxy, which receives from the server and from the client suitable data for this purpose. Alternatively, the round-trip time is determined by the client or by the server, and transmitted to the proxy. For example, a start time at the server and an end time at the client are contained jointly with the frame or the reply in a packet, and are evaluated by the proxy.

In an embodiment having dynamic limiting, the subset of frames that is forwarded is defined by an adjustable factor, which specifies a number of successive frames, of which, one is forwarded and all the others are discarded. The frame rate is now adapted according to the round-trip time by increasing the factor by 1 if the round-trip time exceeds an upper threshold value, and decreasing by 1 if the round-trip time goes below a lower threshold value.

The default value of the factor preferably equals 1, so that every frame from the server is transferred to the client. If the round-trip time exceeds the upper threshold value, the factor is incremented in integer steps to a value X, so that only every Xth frame is still forwarded to the client and the remaining frames are discarded. Conversely, the factor is decremented in integer steps if the round-trip time goes below the lower threshold value. In a suitable embodiment, the factor is incremented until the round-trip time lies above the upper threshold value and is kept constant if the round-trip time lies below the upper threshold value. The same applies to the lower threshold value and reducing the factor, with 1 being the lowest possible value that the factor can take, in which case the frame rate of the server is supported in full by the client.

Irrespective of whether static or dynamic limiting is taking place, the frames that are not forwarded by the proxy to the client may be flagged as discarded in a reply to the server.

When there are a plurality of servers, including a plurality of virtual servers, that are presented jointly on one client (e.g., in general, when there are a plurality of data streams for one client), it is advantageous to have bandwidth control in which unnecessary data streams are disabled, thereby additionally saving bandwidth and relieving the load on the internal network and the client. In a suitable embodiment, at a given point in time, only some data streams of a plurality of data streams from a plurality of servers are displayed on the client, and the remaining data streams are paused, so that corresponding frames are not transferred to the client, thereby achieving overall a bandwidth reduction. Hence, just the data streams that are not being displayed by the client at that instant (e.g., because the data streams are currently not relevant to the user or not requested by the user, or because their regions are hidden in order to display other regions) are disabled. Frames that are not needed are thus not displayed. For this purpose, the client notifies the server which data streams are actually being displayed, and the server disables all the data streams that are not being displayed (e.g., the transfer of frames in these data streams is paused).

In another embodiment, the proxy transcodes the frames that are forwarded from the server to the client such that their size is reduced in order to take up less bandwidth in the internal network and to relieve the load thereon accordingly. If the frames have already been compressed by the server, the proxy performs a further reduction in the volume of data. If the frames from the server are uncompressed, the frames are now compressed by the proxy.

For the connection from the server to the client via the proxy, the proxy or the client, or both, detect a loss of connection by, for example, an activity test. In this test, the proxy or the client, or both, measure the time that has elapsed since the last transmitted frame was received. A loss of connection is ascertained if this time exceeds a predefined threshold value of, for example, 1 s. For a paused connection (e.g., as described above), however, there is no longer any regular transfer of frames even though the connection still exists per se and is usable. In order to prevent a loss of connection being ascertained incorrectly in this case, for a paused connection of this type, a dummy frame that takes up the minimum possible bandwidth (e.g., a single pixel) is regularly transferred instead of an actual frame, thereby keeping the connection active. Keeping the connection active (e.g., using a dummy frame if applicable) is also referred to as a "heartbeat". Conversely, for the connection from the client to the server via the proxy, the server likewise detects a loss of connection using a suitable activity test. For this purpose, the client or the proxy, or both, send a reply to the server as soon as a packet from the server has been received by the proxy or by the client. The server then measures the time until receiving the reply and ascertains a loss of connection if this time exceeds a predefined threshold value of 1 s, for example. The reaction of the server to a loss of connection is defined, for example, by the manufacturer.

Limiting the bandwidth, for example, constitutes adaptive bandwidth management. This is because frames are omitted, less data is sent, and the load on the internal network is reduced based on the processing capacity of the client. This is also advantageous because the transfer of the user interface exists, for example, in parallel with additional and potentially time-critical data traffic. In order to avoid compromising this data traffic, the bandwidth usage is reduced according to need. A costly real-time network or similarly costly Fieldbus hardware for controlling the various streams of frames and other data is not needed, and may even be dispensed with.

In summary, the method and the transfer protocol employed therein provide various ways in which to monitor the transfer between a server and a client. Earlier statements describe, for example, the facility to determine a transfer rate for data, to monitor a data handover, to perform an activity test, to ascertain a loss of connection, to measure a round-trip time, to measure at the client, proxy, or server end, the latency in the transfer of data, to measure a difference between real-time clocks as a time base for virtual clocks in the servers, and to synchronize the proxy, the server, and the client, and to monitor recurring refreshes. Thus, one or more of the following pieces of information is available to a server for reacting according to the embodiment: the bandwidth of the external network; which client of a plurality of clients is the slowest; the result of a test of activity (e.g., a "heartbeat"); a round-trip time between the server and a particular client; a relative or absolute frame latency, or both; information as to whether and which frames have been discarded in the transfer to a particular client; information as to whether there was a delay in a client receiving a frame (e.g., because the relative latency has exceeded a threshold value or there was another reason for a slowdown). These facilities and pieces of information all share the advantage that by being used or employed, a functional risk generally of a delayed transfer and specifically of a delayed display of a user interface of a server on a client is mitigated significantly or even eliminated. This results in improved functional safety when using a particular server.

In one embodiment, the frame integrity (e.g., the integrity of the individual frames) is also monitored in the method in accordance with the transfer protocol. This is done by sending as part of each packet also a checksum (e.g., CRC32) that is checked by the client. If the client ascertains a discrepancy in the checksum, the frame is not displayed and is labeled as faulty in the associated reply to the server. This integrity check of the frame data is advantageous especially with UDP as the transport layer.

The user interface that is output by the server is specified, for example, by the server manufacturer. The client scales the user interface suitably as required to a display area that has been defined for this purpose by the client or by the proxy, and also scales any input area accordingly. An embodiment is also suitable in which the server itself scales its user interface to a display area of the client. In one embodiment, the server already supports the frame resolution used by the client (e.g., 1280×720 pixels) in order to obtain a depiction on the client that is as true to the original as possible.

The client is configured to display a plurality of user interfaces jointly (e.g., side-by-side) and thereby implement a parallel display. An embodiment having a hybrid display may be provided. In this embodiment, a display area of the client is divided into two display regions (e.g., a first region for the user interface of the master device, for its own internal display, and a second region for the user interface of one or more servers, for the external display). The user interfaces of the servers and of the master device then form what are effectively subunits of a master GUI and may be used altogether from a central location. The client may be configured to display in the second region the user interface of a particular server according to need (e.g., just when the user is meant to interact with the server). The second region may be switched between the internal display and the external display so that the entire display area of the client may be used for interacting with the master device, and is switched over as necessary for interacting with a server. In the case of a multicomponent master device, this embodiment may be used for a monitor of the main device.

The hybrid display is advantageous when using a medical imaging device as the master device, because in this case, certain information may have to be displayed permanently for regulatory reasons (e.g., relating to a radiation source). In this case, such information is, for example, the activity status of the radiation source, the voltage thereof, current, dose, and radiation time. This information is then displayed permanently in the first region, while other information is displayed alternately according to need in the second region. The same applies analogously to any information from a server that may have to be displayed permanently. In the case of a multicomponent master device, the hybrid display may be used for the monitors of the auxiliary device.

A client having a hybrid display may be configured such that queries from the master device to the user are displayed in the form of dialog windows in the second region, and are then superimposed at least temporarily on the external display there (e.g., until the necessary input is made). As a result, an enlarged display area is provided for interacting with the master device, and therefore, the first region for the internal display may be configured with correspondingly space-saving dimensions and accordingly also significantly smaller dimensions than the second region for the external display. For example, the first region then contains mainly, or solely, the above-described information to be permanently displayed, whereas optional interactions are only displayed as required and then made in the second region.

The client may be equipped with a convenience function to reduce unnecessary interactions by the user as far as possible. This concerns, for example, the cases in which an interaction with a server simultaneously also requires a certain interaction with the master device. In this case, as part of the convenience function, the display fields and input fields of the user interface of the master device that are needed for the interaction with the server are displayed jointly with the user interface of the server, and may even be integrated therein. The output fields and input fields of the master device that are needed are requested, for example, by the server.

Another advantage is, for example, that a plurality of servers may be connected to a plurality of clients, and thereby, a plurality of devices may be controlled as a bundle via a single master device including a plurality of clients for displaying the user interfaces. In this case, not only are the user interfaces of a plurality of servers presented simultaneously and independently of one another by the clients, but the inputs for the servers may also be made from the clients simultaneously and independently of one another. The proxy mediates in this process between a plurality of clients, for example, such that during an input via one of the clients, an additional input via the other clients is disabled. A server may thus only be controlled via one client at any one point in time. This may prevent passing the control from one client to another client.

In the case of a plurality of servers, each server is, for example, a standalone medical device in its own right, having at least one specific clinical function. Each server typically includes a dedicated output device for the output of information, and an input device for control. A plurality of servers may accordingly be distinguished physically from one another, and accordingly constitute a plurality of separate medical devices. Alternatively or additionally, a server having a plurality of instances is operated, so that the server effectively includes a plurality of virtual devices having a corresponding number of user interfaces, which are then displayed simultaneously by the clients and are used there for controlling the virtual devices.

In the case of a plurality of clients, each client is configured to display at least one user interface and to interact therewith. For this purpose, the client includes an output device in order to display the user interface and thereby to output information. The output device may be a monitor. For the purpose of interaction, the client also further includes an input device in order to input control commands. The input device is a keyboard or mouse, for example. In an embodiment, the client includes a touchscreen that is both output device and input device at once and allows direct interaction with the user interface. The touchscreen is configured for single-touch or multi-touch input.

The server, the proxy, and the clients each constitute a communication node of an overall network that also contains the internal network and the external network. Each communication node is configured, for example, for autonomous implementation of the transfer protocol, and, for example, also performs error correction or a restart after an error or a connection fault autonomously (e.g., independently of the other communication nodes). In such a process, a suitable indicator may be output to the user (e.g., that in this situation, reliable transfer is not guaranteed).

Each server, for example, provides its own connection parameters, which, for example, include frame resolution, frame encoding, frame format, or any combination thereof, with the result that in an embodiment, a plurality of servers are operated with different connection parameters. It is thereby possible for different devices (e.g., from different manufacturers) to be combined with one another and to be controlled jointly by the master device.

For example, loss-less or lossy encoding is used for the transfer. Depending on the use and bandwidth that is available, the frames are compressed in a loss-less or lossy manner. This is specified, for example, by the server, because the server intrinsically knows for what it is used and thus is best placed to decide whether or not a lossy compression is admissible and acceptable. The transfer protocol optionally uses encryption and corresponding authentication. The transfer protocol and, for example, also the proxy, which constitutes an interface of the master device to the outside world, may be configured to be as robust as possible to typical faults in the external network (e.g., delays, packet loss, data loss, resending data, hacker attacks, and the like).

In one embodiment, a handshake is needed for each connection of a server to the master device. The handshake is used by the server to signal that the server supports the specific transfer protocol. A version number of the transfer protocol is, for example exchanged in the handshake. Optionally, in the handshake, one or more other parameters are also exchanged (e.g., identification information such as a device ID or a serial number, license information, symbols, graphics or texts), for example, in order to represent usage of the server on the client by a special icon or label.

The interaction with a server via a client is may also be dependent on the existence of a use license, which is stored on the server and is transmitted by the server (e.g., as license information) in the handshake in order to allow a transfer of the user interface. The proxy may perform a watchdog function to prevent the possibility of dangerous or hostile access to the internal network from the external network. For example, the proxy also supports the handshake of the server, specifically for the purpose of authentication and encryption. In one embodiment, any communication (e.g., transfer of data) between server and client takes place exclusively via the proxy.

DETAILED DESCRIPTION

Figure 1:
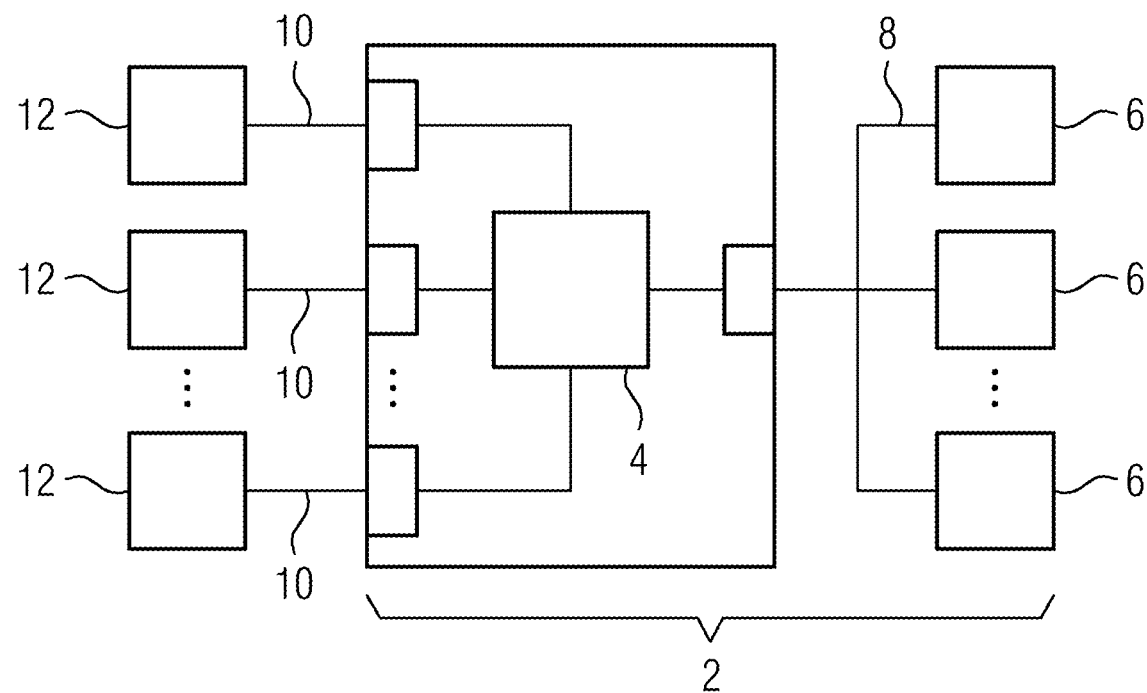
FIG. 1 shows a proxy, a plurality of servers, and a plurality of clients.

FIG. 1 shows one embodiment of a master device 2 (e.g., a medical imaging device, such as a C-arm machine). The master device 2 includes a proxy 4 and a plurality of clients 6 that are connected to one another via at least one internal network 8. The proxy 4 forms an interface of the device 2 to the outside and, in this case, is connected via at least one external network 10 to a plurality of servers 12, each of which is a standalone medical device. The statements relating to this arrangement apply analogously also to embodiments (not shown) including just one server 12 or just one client 6. The internal network 8 is, for example, a TCP/IP network. The external network 10 is, for example, based on a wired standard Ethernet. In one variant, at least one of the networks 8, 10 is wireless. All the data that is transferred from a server 12 to a client 6, or vice versa, passes through the proxy 4.

The clients 6 are each embodied in FIG. 1 as a touchscreen in order to also display one or more user interfaces 14 of one or more servers 12 as an alternative to, or in combination with, a user interface 14 of the master device 2 itself. The embodiment as a touchscreen is not essential. In one variant, a client 6 includes a monitor merely for display and, for example, a mouse or keyboard as input devices. A combination of touchscreen with another input device may also be provided. The master device 2 is formed from, for example, multiple components and has a main unit that includes the proxy 4, one of the clients 6, a C-arm (not shown), and also an auxiliary unit that includes the remaining clients 6. The servers 12 are likewise medical devices, although, for example, from another manufacturer. One of the servers 12 is a navigation device, for example.

In the present case, each server 12 and the master device 2 include a user interface 14 (e.g., a graphical user interface (GUI)). The user interfaces 14 of the servers 10 are transferred via the proxy 4 to the clients 6 and displayed there. The user interface 14 of each server 12 may thus be presented simultaneously on each of the clients 6, and conversely, a plurality of servers 12 may analogously also be controlled from a single client 6. Each client 6 is designed to display jointly a plurality of user interfaces 14.

Figure 2:
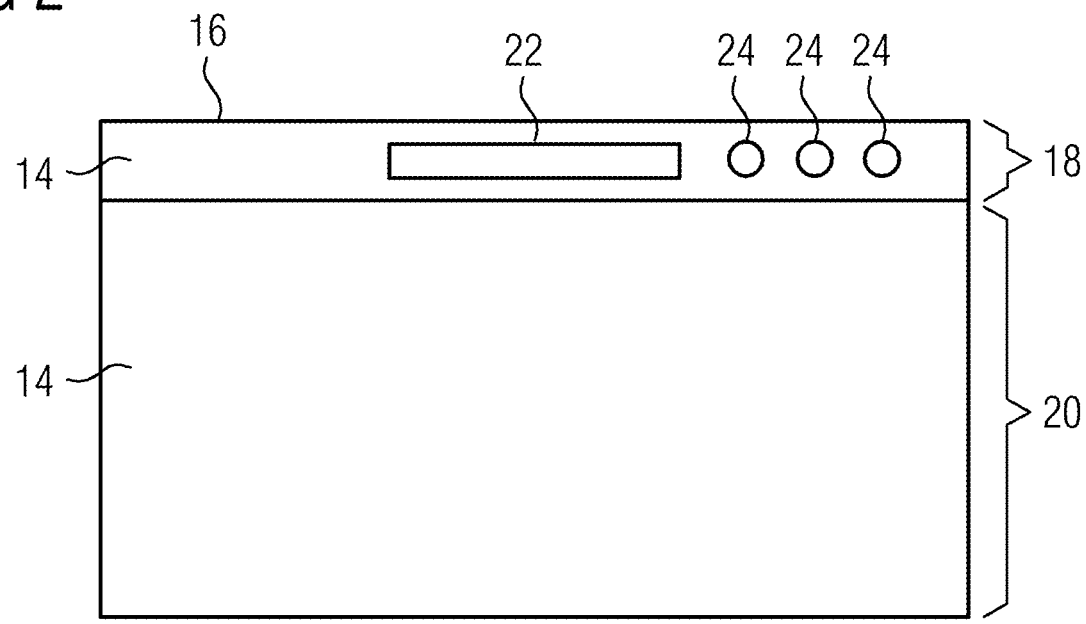
FIG. 2 shows an exemplary display on a client.
Figure 3:
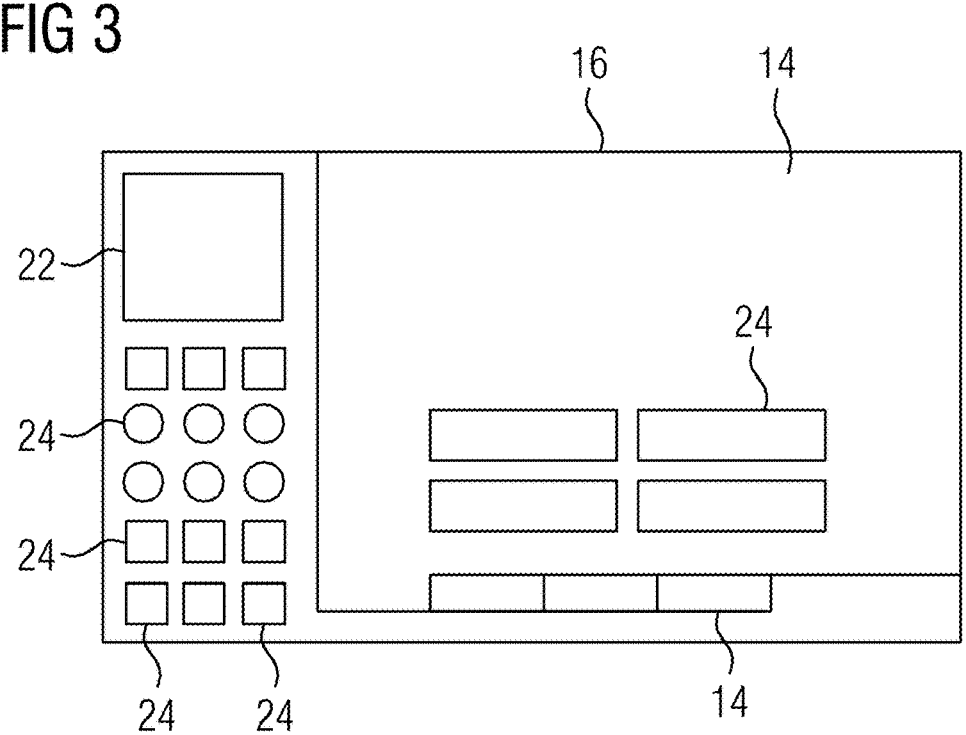
FIG. 3 shows another exemplary display on a client.

FIG. 2 shows an example of a display of a client 6 (e.g., a hybrid display), in which a display area 16 of the client 6 is divided into two display regions 18, 20 (e.g., a first region 18 for the user interface 14 of the master device 2 (at the top edge of the display area 16 in FIG. 2) and a second region 20 for the user interface 14 of one or more servers 12 (below the first region 18 in FIG. 2)). In the second region 20, the user interface 14 of a particular server 12 is now displayed according to need, specifically just when a user is meant to interact with the server 12. The second region 20 may also be switched over, however, to display an extended user interface 14 of the master device 2. FIG. 3 shows a variant of the display (e.g., on another of the clients 6). In this case, the second region 20 may be accessed via a tab.

Figure 4:
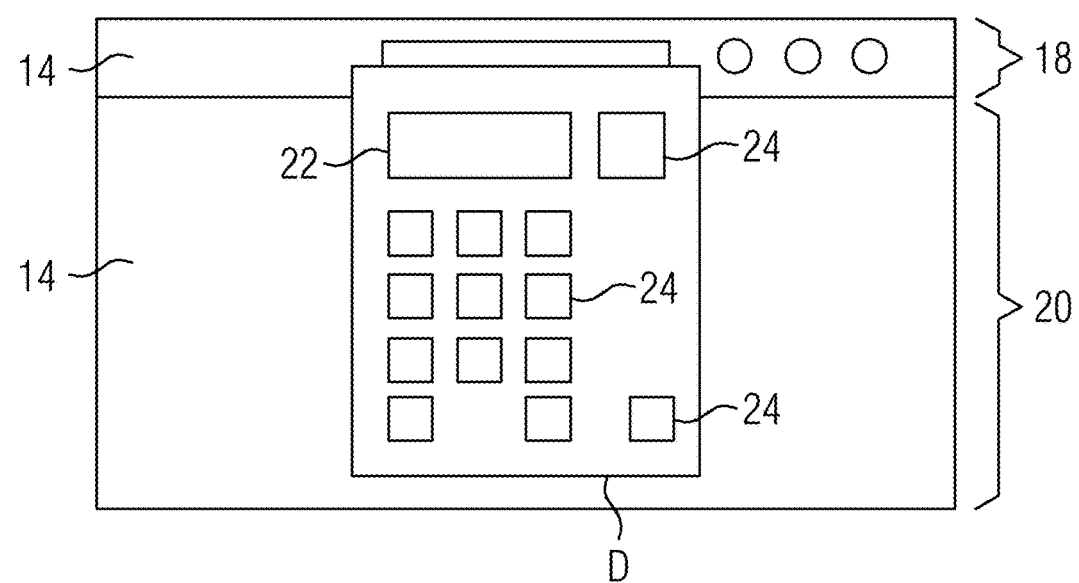
FIG. 4 shows another exemplary display on a client.

FIG. 4 shows, on the basis of FIG. 2, that the client 6 having a hybrid display is additionally designed such that queries from the master device 2 to the user are displayed in the form of dialog windows D in the second region 20, and are then superimposed at least temporarily (e.g., until the necessary input is made) on any external display that may be displayed there. As a result, an enlarged display area is provided for interacting with the master device 2.

For the purpose of transferring a user interface 14 from a server 12 via the proxy 4 to a client 6, a specific method that implements a specific transfer protocol is used in order to bring about a particularly reliable transfer of the user interface 14 in a simplest possible standard network by latency monitoring at the frame buffer level. The latency monitoring is defined in a protocol.

According to the method, the first principle is that a user interface 14 of the server 12 is transferred to the clients 6 such that the user interface 14 is displayed on the client 6, and the server 12 may be controlled from the client 6. It is thus possible for a user to use the client 6 to control the server 12 and, conversely, to transmit information from the server 12 to the client 6 and output the information via the client. In general, interaction with the server 12 (e.g., both display and input) is possible from the client 6. As shown in FIGS. 2 to 4, the user interface 14 typically includes display fields 22 for presenting information and control fields 24 for inputting control commands. The specific embodiment of the user interface 14 depends on the device 2, 12.

According to the method, in order to display the user interface 14 on the client 6, a data stream of a plurality of successive frames 26 is transmitted from the server 12 to the client 6 by a packet-based transfer. This is done in the present case in the form of packets, where it is assumed here without loss of generality that each packet contains exactly one frame 26. The data stream accordingly consists of a plurality of successive frames that are sent at a frequency equal to a frame rate of the server 12. In addition to a frame 26, a packet also contains other data (e.g., a frame number).

The packet-based transfer is bidirectional in the present case. This is shown in FIGS. 5 to 8. A server 12 sends a packet containing a frame 26 and other data via the proxy 4 to the clients 6, which after receiving the packet, send back a reply 28, likewise a packet, to the server 12 via the proxy 4. The reply 28 contains the frame number, so that the server 12 is able to associate the reply 28 with a previously sent packet.

According to the method, a latency AFL, IFL of the transfer is determined recurrently at each client 6 on receiving individual frames 26 in order to monitor the transfer. This monitoring of the receipt of the individual frames 26 provides that the latency AFL, IFL of the transfer is monitored at the frame buffer level. For this purpose, in the present case, the receipt of a frame 26 by a client 6 is used as the trigger for determining the latency AFL, IFL (e.g., is used recurrently), so that the latency AFL, IFL is determined continuously and measured in the process at a frequency that lies in the region of the frame rate of the server 12 and the clients 6.

Determining the latency AFL, IFL is used to, for example, detect particularly quickly a slowdown in the transfer via the networks 8, 10, or an overload of a client 6, and to trigger a suitable reaction thereto by the sever 12, the proxy 4, or the client 6. A reaction is triggered, for example, when the latency AFL, IFL exceeds a specified threshold value. The latency AFL, IFL is determined by the client 6, by the proxy 4, by the server 12, or any combination thereof. The information needed to do this is obtained from the data stream or, more precisely, from the individual packets. In the embodiment shown including a plurality of servers 12 and a plurality of clients 6, the latency AFL, IFL is detected individually for each individual connection between one of the servers 12 and one of the clients 6, and thus individually for each data stream.

The determination of the latency AFL, IFL is defined in a protocol (e.g., by a transfer protocol), and therefore, there are no specific requirements made of the hardware. The method is performed using particularly low-cost and simple standard technology. At least in the external network 10, the user interface 14 is transferred in a wired or wireless manner via a low-cost, packet-based network (e.g., standard Ethernet, WLAN, or suchlike) and not via a special real-time Ethernet. The internal network 8 is based on, for example, TCP/IP technology. The transfer protocol is also used to transmit control commands to the server 12 concerned via a corresponding return channel.

In the present case, the latency AFL, IFL is determined by the client 6 and also used by the client to adjust suitably behavior of the client with respect to the user. Specifically, the user is informed, for example, about transfer problems, or an input via the client 6 is disabled for direct prevention of input mistakes. Also, inputs that are in progress are interrupted if the threshold value is exceeded. The threshold value may be adjusted and is stored in a memory of the client 6. On a threshold value being exceeded, a suitable indicator (e.g., a text) is also output, warning that the latency AFL, IFL has exceeded the threshold value and the displayed user interface 14 therefore may no longer be live. For example, the text is displayed as a semitransparent overlay of the user interface 14.

Figure 5:
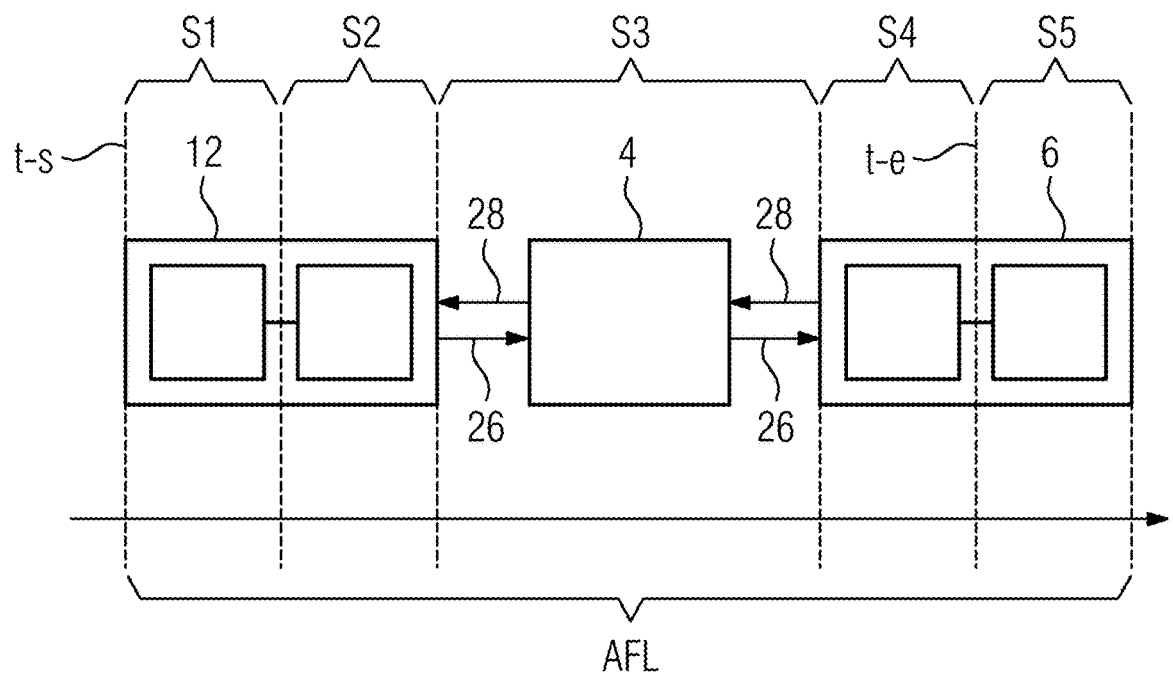
FIG. 5 shows exemplary determination of an absolute frame latency.
Figure 6:
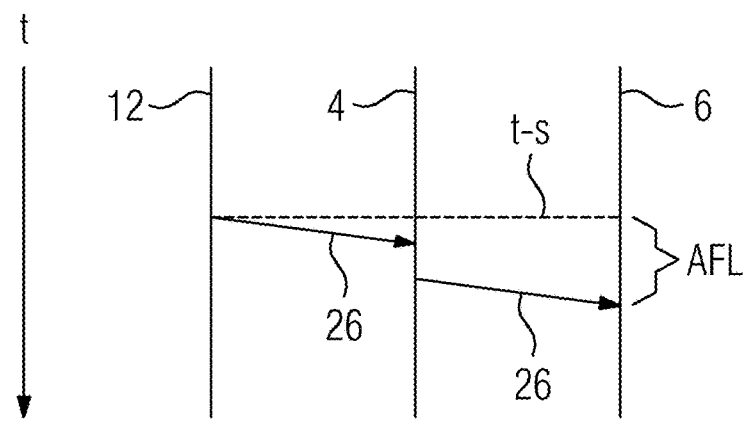
FIG. 6 shows an example of a client determining an absolute frame latency.
Figure 7:
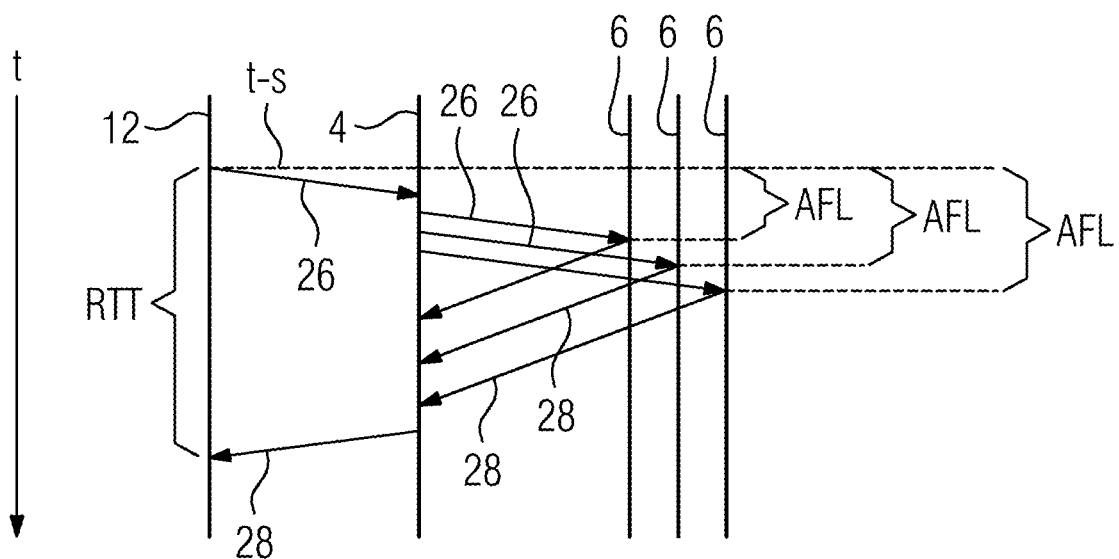
FIG. 7 shows exemplary determination of an absolute frame latency given a plurality of clients.
Figure 8:
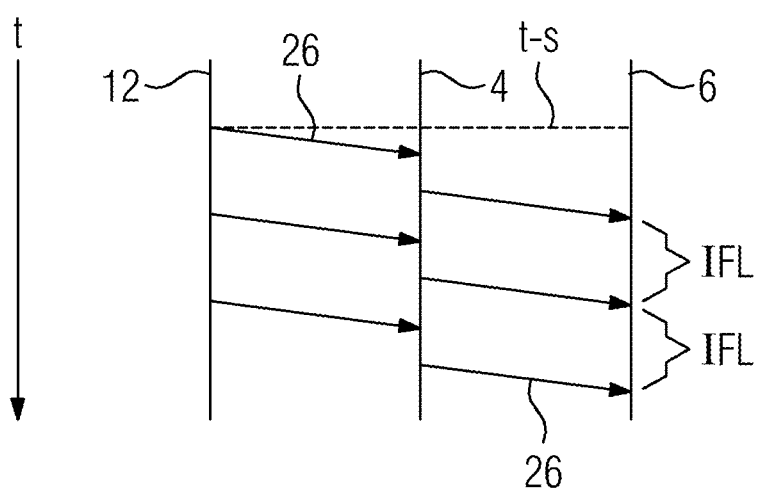
FIG. 8 shows exemplary determination of a relative latency.

FIGS. 5 to 8 show various exemplary strategies for determining the latency AFL, IFL. FIG. 5 shows a simplified representation of the architecture of FIG. 1 having a time axis for a time t, and in each of FIGS. 6 to 8, the time t is plotted in the vertical direction and the connection from a server 12 via a proxy 4 to one or more clients 6 is in the horizontal direction. In FIGS. 5 to 7, an absolute frame latency AFL is determined. In FIG. 8, a relative latency IFL is determined by the client.

When transferring a particular frame 26, the server 12 also sends a time stamp that indicates a start time t-s of the server-side processing of the frame 26 (e.g., the start of reading S1 the frame 26 from a frame buffer of the server 12). The client-side processing of the frame 26 is divided into a receive process S4 and a display process S5 for the frame 26. The display process S5 does not start until the receive process S4 has finished. The absolute frame latency AFL is then determined as the sum of two time segments (e.g., a first time segment that extends from the start time t-s until the end of the receive process S4, which is denoted by an end time t-e that is suitably ascertained, and a second time segment that defines a time length of the display process S5). The end time t-e may be ascertained by the client 6 after receipt of the particular frame 26.

The absolute frame latency AFL is thus obtained, as shown in FIG. 5, from the following, successively executed acts S1 to S5. First, a server-side read process S1 is performed for a frame 26 (e.g., reading (grabbing) the frame 26 from the frame buffer of the server 12). Second, the method includes compressing S2 the frame 26, although this is optional. Third, the method includes packet-based transfer S3 of the frame 26 from the server 12 via the proxy 4 to the client 6. Fourth, the client 6 receives and decodes S4 the frame 26. Fifth, the method includes displaying S5 the frame 26 on the client 6. The first and second acts S1, S2 are elements of the server-side processing of the frame 26. The third act S3 denotes the transfer between the server 12 and the client 6 via the proxy 4 and the various networks 8, 10. The fourth and fifth acts S4, S5 are elements of the client-side processing of the frame 26, where the fourth act S4 corresponds to the receive process of the client 6, and the fifth act S5 corresponds to the display process. Each of these acts has a certain time length, and the sum of these time lengths gives the absolute frame latency AFL.

The time length from the start of the first act S1 to the end of the fourth act S4 is calculated from the start time t-s and the end time t-e, and hence calculated entirely in software. The determination of the time length of the fifth act S5 (e.g., of the display process) is either stored as a predefined offset in a memory or is measured by the client 6 for a particular frame 26, or both, and then added on accordingly. The offset is determined in advance, for example, by suitable tests and measurements, and then retrieved during operation. In order to measure the time length of the display process S5 during operation, the client 6 is operated with a special display driver that continuously measures the time length of the display process S5 for a particular frame 26.

In a development that is not shown, in addition to the absolute frame latency AFL, an interaction latency is also determined, which precedes the previously described absolute frame latency AFL, and defines the time length required for an input by the user at the client 6 to lead to a change in the user interface 14 at the server 12.

When there are a plurality of clients 6, it is possible that different absolute frame latencies AFL also arise for the different data streams. FIG. 7 shows how the proxy 4 evaluates the absolute frame latencies AFL of a plurality of clients 6 with respect to a server 12, and uses a maximum comparison to determine the largest absolute frame latency AFL, which is then transferred to the server 12, so that the server may react appropriately. As shown in FIG. 7, the absolute frame latency AFL is transmitted in the reply 28 to the server 12, which calculates therefrom, in conjunction with a time of arrival of the reply 28 at the server 12, a round-trip time RTT for the transfer between server 12 and client 6. The round-trip time RTT is obtained, for example, as the sum of the largest absolute frame latency AFL and the time taken for the reply 28 of the slowest client 6 to reach the server 12.

In order to determine the start time t-s and the end time t-e, the server 12 and the client 6 each include a real-time clock (not shown). When a connection is being established, the server 12 initializes a monotonically incrementing counter, which is also used to generate the time stamps. This implements a virtual clock, which the proxy 4 uses for synchronization when a connection is being established and recurrently while the connection is in place. The proxy 4 identifies therefrom a relative divergence of a time from the time of the server 12. The same applies to the client 6. Actual synchronization of the real-time clocks is dispensed with. Each relative divergence is averaged over a plurality of measurements.

The relative latency inter-frame latency (IFL) is defined as the time t between two successive frames (e.g., as shown in FIG. 8). The relative latency IFL is obtained, for example, as the difference between the arrival times of two successive frames 26 at the client 6. The client 6 thereby detects whether the display is being refreshed regularly or whether the transfer is frozen or halted. This implements an activity test, by which a loss of connection is detected if the relative latency IFL exceeds a suitable threshold value of, for example, 1 s.

The data stream generated by a server 12 may be too large for the internal network 8 or the client 6, or both. In order to prevent overloading the bandwidth of the network or overloading a client 6 that has a lower performance than the server 12, bandwidth control is performed, in which the number of frames 26 and hence the size of the data stream between server 12 and client 6 is controlled, for example, by the proxy 4. This reduction in the frame data also prevents disruption to the transfer of other data, and therefore, there is no need for additional quality of service on the part of the networks 8, 10.

Figure 9:
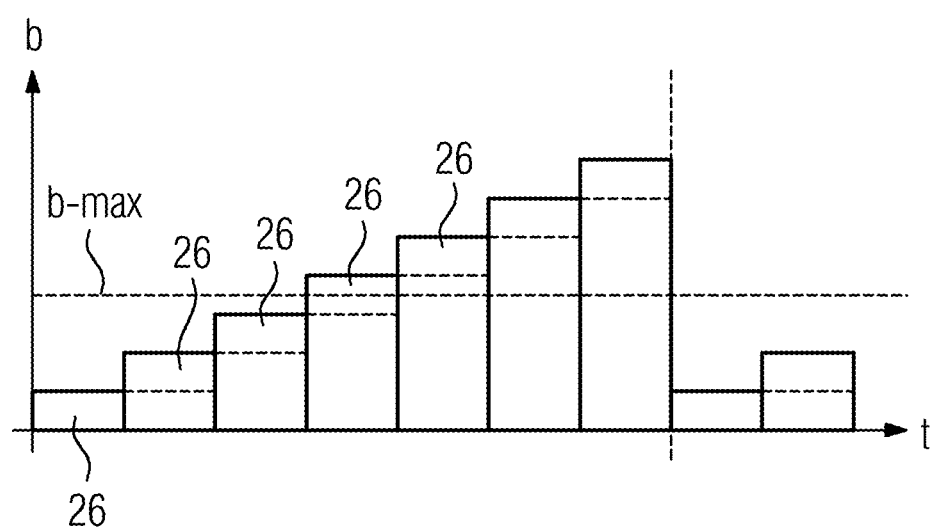
FIG. 9 shows an exemplary static bandwidth-reduction.
Figure 10:
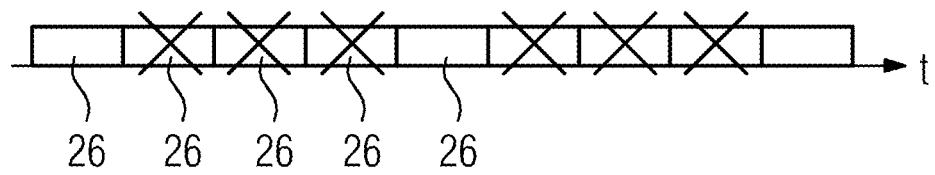
FIG. 10 shows an exemplary dynamic bandwidth-reduction.

FIGS. 9 and 10 depict two strategies for limiting the bandwidth (e.g., static bandwidth-limiting in FIG. 9 and dynamic bandwidth-limiting in FIG. 10). Each figure shows the sent frames 26 as a function of time t. In the present case, the two strategies are combined such that dynamic limiting is used if a defined frame rate for the client 6 concerned is not stored in the proxy 4 for the purpose of static limiting.

FIG. 9 shows the bandwidth b summated for successive frames 26 within a time segment t1 as a function of time t. In general, the server 12 sends the frames 26 at a frame rate that is limited by the proxy 4, as shown in FIG. 9, to a maximum bandwidth b-max of the internal network 8, by the proxy 4 forwarding frames 26 to the client 6 within a given time segment t1 only until the maximum bandwidth b-max is reached. None of the subsequent frames 26 within the time segment t1 (e.g., 1 s) are forwarded to the client 6. Hence, effectively, a rolling summation of the volume of frame data being transferred is performed, and frames 26 are omitted when this volume of data exceeds an upper limit. The volume of data that accumulates in the time segment t1 is illustrated in FIG. 9 by the increasing size of the bars. The proxy 4 does not forward the discarded frames 26 to the client 6, but it is flagged in the reply 28 to the server 12 as to whether the associated frame 26 has been discarded, so that the server 12 may react accordingly depending on the embodiment.

With dynamic limiting as shown in FIG. 10, the frames 26 from the server 12 are forwarded by the proxy 4 at a frame rate that is adapted dynamically to the processing time of the client 6 by ascertaining a round-trip time RTT between the server 12 and the client 6, and depending on the round-trip time RTT, forwarding only a subset of frames 26 to the client 6. This is illustrated in FIG. 10 by the succession of frames 26 over time, of which only every fourth frame 26 is forwarded to the client 4, and the three intervening frames 26 are discarded. The subset of frames 26 that is forwarded is defined by an adjustable factor, which specifies a number of successive frames 26, of which, one is forwarded and all the others are discarded. In FIG. 10, the factor accordingly equals four, and therefore, only every fourth frame 26 is forwarded. The frame rate is now adapted according to the round-trip time RTT by increasing the factor by one if the round-trip time RTT exceeds an upper threshold value, and decreasing by one if the round-trip time RTT goes below a lower threshold value.

Those frames 26 that are not being displayed by the client 6 at a given point in time, in the present case, are also not transferred from the server 12 in the first place. This is done as part of additional bandwidth control, in which unnecessary data streams for a particular client 6 are disabled, thereby additionally saving bandwidth and relieving the load on the internal network 8 and the client 6 concerned. Alternatively or additionally, the proxy 4 transcodes the frames 26 that are forwarded from the server 12 to the client 6 such that a size is reduced, in order to relieve the load on the internal network 8 further.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for transferring a user interface from at least one server via a proxy to at least one client, the method comprising:
    transferring a user interface of a server of the at least one server to a client of the at least one client such that the user interface is displayed on the client, and the server is controllable from the client;
    transmitting a data stream of a plurality of successive frames from the server to the client by a packet-based transfer, such that the user interface is displayed on the client; and
    determining a latency of the transfer recurrently for individual frames of the plurality of successive frames, such that the transfer is monitored,
    wherein the latency is determined as an absolute frame latency,
    wherein when transferring a particular frame of the plurality of successive frames, the server sends a time stamp that indicates a start time of a server-side processing of the particular frame,
    wherein a client-side processing is divided into a receive process and a display process for the frame, and
    wherein the absolute frame latency is determined as a sum of two time segments.

2. The method of claim 1, wherein the latency is determined as a difference between a start of a server-side processing of a particular frame of the plurality of successive frames and an end of a client-side processing of the particular frame.

3. The method of claim 1, wherein the time stamp includes a start of reading the particular frame from a frame buffer of the server.

4. The method of claim 1, wherein the two time segments include a first time segment that extends from the start time until an end of the receive process, and a second time segment that defines a time length of the display process.

5. The method of claim 4, wherein the time length of the display process is stored as a predefined offset in a memory, or
    wherein the client measures the time length of the display process for a particular frame of the plurality of successive frames.

6. The method of claim 1, wherein the user interface of the server is transferred via the proxy to a plurality of clients, resulting in a dedicated data stream for each client of the plurality of clients,
    wherein each client of the plurality of clients determines the absolute frame latency for the associated data stream, and wherein the proxy determines a largest absolute frame latency and transmits the largest absolute frame latency to the server.

7. The method of claim 1, wherein the latency is determined as a relative latency between two successive frames of the plurality of successive frames.

8. The method of claim 1, wherein the client determines the latency and compares the latency with at least one threshold value, and
wherein the client outputs an indicator, disables the user interface of the server on the client, or outputs the indicator and disables the user interface of the server on the client when the latency exceeds the threshold value.

9. The method of claim 1, wherein the client determines the latency and transmits the latency to the server in a reply, such that the server is allowed to react to the latency.

10. The method of claim 1, wherein the server sends the plurality of successive frames at a frame rate that is limited by the proxy to a maximum bandwidth by the proxy forwarding frames to the client within a given time segment only until the maximum bandwidth is reached, and not forwarding to the client any of subsequent frames within a time segment.

11. The method of claim 1, wherein the plurality of successive frames from the server are forwarded by the proxy at a frame rate that is adapted dynamically by ascertaining a round-trip time between the server and the client, and depending on the round-trip time, forwarding only a subset of frames of the plurality of successive frames to the client,
wherein the subset of frames that is forwarded is defined by an adjustable factor that specifies a number of successive frames, of which one is forwarded and all others are discarded, and
wherein the adjustable factor is increased by one when the round-trip time exceeds an upper threshold value, and is decreased by one when the round-trip time goes below a lower threshold value.

12. The method of claim 1, wherein at a given point in time, only some of a plurality of data streams from a plurality of servers are displayed on the client, and the remaining data streams of the plurality of data streams are paused, so that frames are not transferred to the client, the plurality of servers including the server.

13. The method of claim 1, wherein the proxy is connected via an external network to the server or to a plurality of servers, the plurality of servers including the server, and wherein the network is a standard Ethernet network or a WLAN network.

14. The method of claim 1, wherein the server is a first medical device,
wherein the proxy and the client are both part of a second medical device, and
wherein the client is a monitor, so that a user interface of the first medical device is looped through to a monitor of the second medical device such that the first medical device is controllable from the second medical device.

15. A medical device comprising:
a proxy; and
a client,
wherein the medical device is configured to:
transfer a user interface of a server to the client such that the user interface is displayed on the client, and the server is controllable from the client;
transmit a data stream of a plurality of successive frames from the server to the client by a packet-based transfer, such that the user interface is displayed on the client; and
determine a latency of the transfer recurrently for individual frames of the plurality of successive frames, such that the transfer is monitored, and
wherein the client is configured to determine the latency and transmit the latency to the server in a reply, such that the server is allowed to react to the latency.

16. A server comprising:
a processor configured to transfer a user interface from at least one server via a proxy to at least one client, the transfer comprising:
transfer of a user interface of a server of the at least one server to a client of the at least one client such that the user interface is displayable on the client, and the server is controllable from the client; and
transmission of a data stream of a plurality of successive frames from the server to the client by a packet-based transfer, such that the user interface is displayable on the client,
wherein the at least one client is configured to determine a latency of the transfer recurrently for individual frames of the plurality of successive frames and transmit the latency to the server in a reply, such that the transfer is monitored and the server is allowed to react to the latency.

17. A method for transferring a user interface from at least one server via a proxy to at least one client, the method comprising:
transferring a user interface of a server of the at least one server to a client of the at least one client such that the user interface is displayed on the client, and the server is controllable from the client;
transmitting a data stream of a plurality of successive frames from the server to the client by a packet-based transfer, such that the user interface is displayed on the client; and
determining a latency of the transfer recurrently for individual frames of the plurality of successive frames, such that the transfer is monitored,
wherein the client determines the latency and compares the latency with at least one threshold value, and
wherein the client outputs an indicator, disables the user interface of the server on the client, or outputs the indicator and disables the user interface of the server on the client when the latency exceeds the threshold value.

18. A method for transferring a user interface from at least one server via a proxy to at least one client, the method comprising:
transferring a user interface of a server of the at least one server to a client of the at least one client such that the user interface is displayed on the client, and the server is controllable from the client;
transmitting a data stream of a plurality of successive frames from the server to the client by a packet-based transfer, such that the user interface is displayed on the client; and
determining a latency of the transfer recurrently for individual frames of the plurality of successive frames, such that the transfer is monitored,
wherein the client determines the latency and transmits the latency to the server in a reply, such that the server is allowed to react to the latency.

19. A method for transferring a user interface from at least one server via a proxy to at least one client, the method comprising:

transferring a user interface of a server of the at least one server to a client of the at least one client such that the user interface is displayed on the client, and the server is controllable from the client;

transmitting a data stream of a plurality of successive frames from the server to the client by a packet-based transfer, such that the user interface is displayed on the client; and determining a latency of the transfer recurrently for individual frames of the plurality of successive frames, such that the transfer is monitored, wherein the server sends the plurality of successive frames at a frame rate that is limited by the proxy to a maximum bandwidth by the proxy forwarding frames to the client within a given time segment only until the maximum bandwidth is reached, and not forwarding to the client any of subsequent frames within a time segment.

20. A method for transferring a user interface from at least one server via a proxy to at least one client, the method comprising:

transferring a user interface of a server of the at least one server to a client of the at least one client such that the user interface is displayed on the client, and the server is controllable from the client;

transmitting a data stream of a plurality of successive frames from the server to the client by a packet-based transfer, such that the user interface is displayed on the client; and determining a latency of the transfer recurrently for individual frames of the plurality of successive frames, such that the transfer is monitored, wherein the plurality of successive frames from the server are forwarded by the proxy at a frame rate that is adapted dynamically by ascertaining a round-trip time between the server and the client, and depending on the round-trip time, forwarding only a subset of frames of the plurality of successive frames to the client, wherein the subset of frames that is forwarded is defined by an adjustable factor that specifies a number of successive frames, of which one is forwarded and all others are discarded, and wherein the adjustable factor is increased by one when the round-trip time exceeds an upper threshold value, and is decreased by one when the round-trip time goes below a lower threshold value.

* * * * *